United States Patent [19]
Mäyrä-Mäkinen et al.

[11] Patent Number: 5,658,748
[45] Date of Patent: Aug. 19, 1997

[54] STREPTOCOCCUS THERMOPHILUS STRAINS AND THEIR USE

[75] Inventors: Annika Mäyrä-Mäkinen; Mervi Sibakov, both of Helsinki; Soile Tynkkynen, Espoo, all of Finland

[73] Assignee: Valio Oy, Helsinki, Finland

[21] Appl. No.: 291,570

[22] Filed: Aug. 16, 1994

[30] Foreign Application Priority Data

Aug. 18, 1993 [FI] Finland .................................. 933643

[51] Int. Cl.$^6$ ............... C12N 1/21; C12Q 1/02; C12Q 1/18
[52] U.S. Cl. ..................... 435/29; 435/32; 435/253.4
[58] Field of Search ................ 435/29, 8, 252.3, 435/253.4, 32

[56] References Cited

U.S. PATENT DOCUMENTS 4,929,456  5/1990  Mayra-Makinen ................. 435/29

FOREIGN PATENT DOCUMENTS

WO90/04037  4/1990  WIPO.

OTHER PUBLICATIONS

Ahmad et al.; "The Production of Bioluminescent Lactic Acid Bacteria Suitable for the Rapid Assessment of Strarter Culture Activity in Milk", Journal of Applied Bacteriology, vol. 70, pp. 113–120 1991.

Mercenier; "Molecular Genetics of *Streptococcus thermophilus*", FEMS Microbiology Reviews, vol. 87, pp. 61–78 1990.

Somkuti et al.; "Genetic Transformation of *Streptococcus thermophilus* by Electroporation", Biochimie, vol. 70, pp. 579–585 1988.

Ahmad et al, "Cloning of the lux genes into *Lactobacillus casei* and *Streptococcus lactis*: phosphate–dependent light production", Biochemical Society Transactions 16:1068 (1988).

Blissett et al, "In vivo bioluminescent determination of apparent $K_m$'s for aldehyde in recombinant bacteria expressing luxA/B", Letters in Applied Microbiology 9:149–152 (1989).

Section 12. Gram–Positive Cocci, Berzey's Manual of Systematic Bacteriology, p. 1048 (1986).

Jacobs et al, "Highly bioluminescent *Streptococcus thermophilus* strain for the detection of dairy–relevant antibiotics in milk", Appl. Microbiol. Biotechnol. 44:405–412 (1995).

*Primary Examiner*—George C. Elliott
*Assistant Examiner*—Amy J. Nelson
*Attorney, Agent, or Firm*—Nixon & Vanderhye P.C.

[57] ABSTRACT

The invention relates to new *Streptococcus thermophilus* strains containing genes giving the bioluminescence property. The strains can be applied widely for analytical purposes, e.g. in the determination of bacteriophages and antibiotics, especially from liquid samples. The invention also relates to a test set containing a bioluminescent *Streptococcus thermophilus* strain, and to processes for the determination of bacteriophages or antibiotics from a liquid sample.

13 Claims, 1 Drawing Sheet

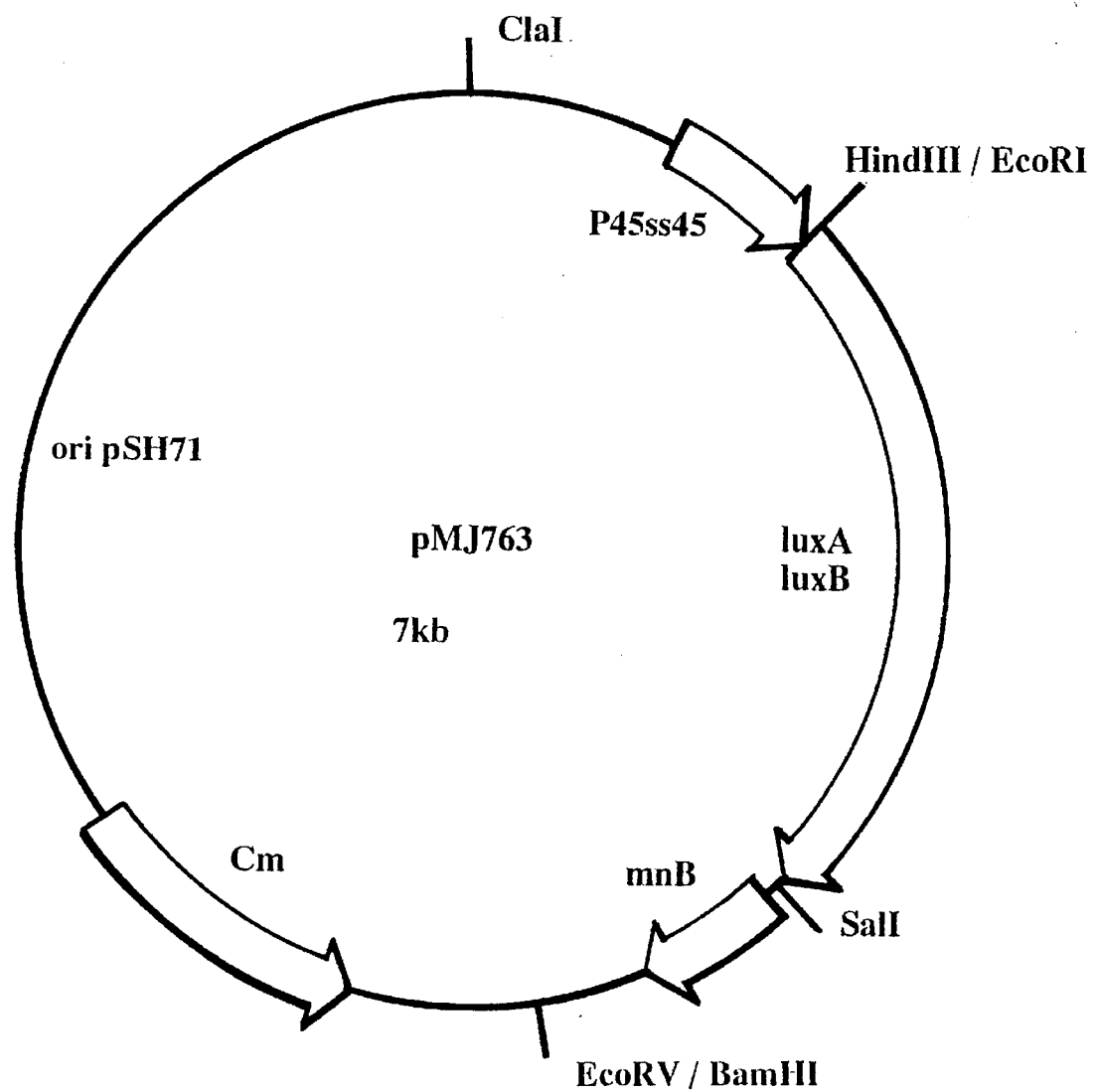

STREPTOCOCCUS THERMOPHILUS STRAINS AND THEIR USE

The invention relates to new *Streptococcus thermophilus* strains containing genes giving the bioluminescence property. The new bioluminescent *Streptococcus thermophilus* strains are very useful tools for various analytical purposes. The strains are suitable e.g. for use in the determination of bacteriophages and antibiotics, particularly from liquid samples. The invention also relates to a test set containing a bioluminescent *Streptococcus thermophilus* strain, and to processes for determining bacteriophages and antibiotics in liquid samples.

In many situations it is of vital importance to be able to detect the presence of small amounts of antibiotics. This is the case in food industries, for instance, where the increased use of antibiotics and chemotherapeutic substances in the treatment of animals has created a need for a simple, reliable and sensitive process of determination. Since antibiotics are also used in the treatment of dairy cows and since antibiotic residues in milk may both cause health hazards and be disadvantageous for food technological reasons, it is especially important to develop processes suitable for an accurate and rapid screening of milk.

Antibiotic residues in milk are generally detected by microbiological processes which utilize the ability of bacteria to produce acid, reduce colours and produce growth on an agar medium. These processes are based on the bactericidal, inhibitory and morphological effect of antibiotics on certain microorganisms.

The Thermocult disk technique is an agar diffusion technique which is widely used in Finland and accepted as an official antibiotic determination procedure. In this technique the test organism is *B. stearothermophilus var. calidolactis*. It has been developed on the basis of an IDF standard process (IDF 1970. Detection of Penicillin in Milk by a Disk Assay Technique. International Standard FIL-IDF 57. Brussels).

A process of corresponding sensitivity is disclosed by van OS et al., Diffusion Test for the Determination of Antibiotic Residues in Milk. Neth. Milk and Dairy J. 29 (1975) 16. The Delvotest process also uses *B. stearothermophilus var. calidolactis* as the test organism. A sample (0.1 ml) is pipetted on agar contained in a vial, and a tablet containing nutrients and a pH indicator is added to the vial. The process is based on the acid producing capability of the test organism. The vials are incubated at 64° C. for 2.5 hours. The evaluation is based on the colour change of the agar layer.

Standard techniques further include the Intertest (BCP-Test). The test microbe used in the process is *Streptococcus thermophilus*. A test tablet containing a lyophilized culture of the test microbe, nutrients, and a pH indicator (bromocresol purple) is added to a milk sample. The incubation time is 4 hours at 45° C. If the sample does not contain any antibiotic, the colour of the solution turns from blue to green and further to yellow. The amount of the antibiotic can be determined to some extent on the basis of the colour by comparing to a colour map (THOROGOOD et al., An Evaluation on the Charm Test—A Rapid Method for the Detection of Penicillin in Milk. J. Dairy Research 50 (1983), 185).

A drawback of these processes is their insufficient sensitivity in view of the needs of milk technology.

FI Patent Specification 75865, corresponding to U.S. Pat. No. 4,929,546, describes a process and a test set based on the use of the *Streptococcus thermophilus* T101 strain. The strain is very suitable for antibiotic determination; it has a very broad spectrum, i.e. it is sensitive to the influence of a wide variety of antibiotics, in addition to which it is far superior in sensitivity to other known microorganisms. The determination is carried out by adding a sample to a test set comprising a *Streptococcus thermophilus* T101 concentrate and a conventional water-based protective agent and optionally a colour indicator; incubating the test set with the sample at 38° to 42° C. for about 4 hours; and evaluating the colour. If the test set does not contain an indicator, this is added in connection with the performance of the test. In the complete test set, bromocresol purple is used as an indicator, whereby the yellow colour indicates a negative result and the blue colour indicates a positive result. Even though the process is far superior in sensitivity to the processes mentioned above, the length of the incubation time is problematic.

The determination of antibiotic residues in milk by chemical or physico-chemical processes is considerably less usual than the use of microbiological processes. Colorimetric and chromatographic processes require skilled labour and often a complicated and expensive analysing equipment. The processes are usually time-consuming and seldom suitable for routine analyses.

The Charm test (CHARM, S. E., A 15-minute Assay for Penicillin and other Antibiotics. Cultured Dairy Products J. 14 (1979) 24) is based on the detection of radioactivity. A lyophilized culture of *B. stearothermophilus* and lyophilized $^{14}C$-labelled penicillin are added to a sample. The amount of $^{14}C$ contained in the bacterium cells is detected by a Geiger counter; the lower the penicillin concentration in the sample, the higher is the reading of the Geiger counter. The determination time is only 15 minutes and the sensitivity of the process is 0.005 I.U. of penicillin per ml. This process, either, is not suitable for routine use; it is expensive and complicated and requires skilled persons and expensive equipment to be carried out.

Accordingly, there is still a need for a rapid sensitive process which has as broad a spectrum as possible with respect to antibiotics. The process should also be simple and preferably allow the use of a ready-to-use assay set.

Bacteriophages constitute another major problem, even in the food industries. Bacteriophages are bacterial viruses that infect the bacteria, proliferate within bacterial cells, and finally cause the lysis of the bacteria. Great numbers of new phages are released in the lysis of bacteria, and these phages in turn may infect other cells of the bacterial population and cause their lysis. Accordingly, even a very small number of infecting bacteriophages may destroy the entire bacterial population in a short time. Bacteriophages may thus cause great disadvantage e.g. in the food industries in fields that use bacteria as starter cultures, such as in the dairy industry in the preparation of sour milk products and especially cheese.

The presence of bacteriophages or infected bacteria in a sample is determined microbiologically by preparing a suspension of said sample and spreading an appropriate dilution of said suspension on an agar plate that has been inoculated with a suspension of bacteria susceptible to the bacteriophage in question. After incubation, the plate has a confluent layer of bacterial growth, except for points where a phage particle or an infected cell has been introduced. Around such points, clear zones, plaques, are formed as a result of the lysis of the bacteria.

Commercial rapid bacteriophage tests for starter cultures used in the food industries are not available. Due to the severe problems caused by bacteriophages, there is an acute need for a sensitive and reliable method which is also simple and rapid.

These advantages are obtained by the present invention, which is based on the creation and utilization of bioluminescence. Bioluminescence means the ability of certain organisms to emit light. The mechanism of light emission and the resulting colour are specific to each organism.

The bioluminescence reaction of bacteria can be represented by the following formula:

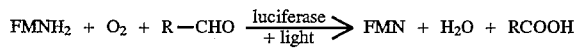

$$FMNH_2 + O_2 + R-CHO \xrightarrow[+ \text{light}]{\text{luciferase}} FMN + H_2O + RCOOH$$

The bioluminescence reaction is catalyzed by luciferase, and the substrates are reduced flavin mononucleotide ($FMNH_2$), a long-chain aldehyde and molecular oxygen. The reaction is highly specific for $FMNH_2$. The aldehyde may be any aldehyde containing 7 to 16 carbon atoms; unsaturated and substituted aldehydes also cause emission of light. Decanal, dodecanal and tetradecanal may be mentioned by way of example.

In the reaction $FMNH_2$ is oxidized into FMN and the aldehyde into a corresponding fatty acid. The energy needed for the light emission is produced mainly in the oxidizing reaction of the aldehyde and $FMNH_2$. The bioluminescence reaction of bacteria produces Greenish-blue light having a maximum wave length of about 490 nm and a quantum efficiency between 0.05 and 0.15.

Bacterial luciferase [EC 1.14.14.3] is a heterodimeric enzyme having a subunit α (about 41 kDa) and a subunit β (about 37 kDa) encoded by the luxA and luxB gene, respectively.

There is a 30% identity between the amino acid sequences of the subunits, and the corresponding genes are assumed to have arisen by gene duplication. A divergence as great as 45% may occur between the sequences of the α unit of luciferases of different bacterium species; with the β units, the divergence may be even greater. At present, the luciferase sequence of about ten different bacterium strains has been determined. By way of example may be mentioned *Vibrio fischeri* and *Photobacterium leiognathi* (Journal of Bioluminescence and Chemiluminescence 4 (1989) 326–341, Baldwin et al.), *Vibrio harveyi* (Journal of Biological Chemistry 260 (1985) 6139–6146, Cohn et al.), and *Xenorhabdus luminescens* (Biochemical and Biophysical Research Communications 170 (1990) 407–415, Johnston et al.).

The genes encoding the luciferase belong to the so-called lux system of bacteria. It has been found that all luminescent bacteria contain five lux genes (luxA–E), which code for the α and β unit of luciferase (luxA and luxB, respectively), the reductase (luxC), transferase (luxD), and synthetase (luxE) of the fatty acid reductase complex. The genes are closely related to each other, and it is assumed that they occur in the same operon in the order luxCDABE. In addition to these genes, other genes closely related to the lux system have been found, which vary depending on the bacterium species and strain. The lux gene system thus varies from one bacterium to another.

Detection processes based on bioluminescence have been developed for both in vitro and in vivo applications. Bacterial luciferase can be used in vitro to detect metabolites which can be transformed into a substrate participating in the reaction. The formation of oxygen and fatty aldehyde can be analyzed in this way. The most important in vitro applications, however, are associated with the monitoring of enzyme reactions which produce either NADH or NADPH or compounds which can be converted into these compounds. Antibodies, antigens and DNA molecules labelled with enzymes may also be determined by bioluminescence. Lux genes have been used in vivo to synthesize luciferase so as to analyze intracellular gene expression and/or metabolism.

Antibiotic determination processes based on bioluminescence have also been developed. Ulitzur (Methods in Enzymology, Vol. 133, (1986), p. 275–284) gives three different processes for the determination of antibiotics by bioluminescence, viz. the lysis test, the induced test, and the bacteriophage test.

The lysis test can be applied to detect antibiotics that affect the cell wall or the cytoplasmic membrane, especially β-lactam antibiotics and polymyxins. According to Ulitzur, the luminescence system of *Photobacterium fischeri* MJ1 has been cloned both in *Escherichia coli* and *Bacillus subtilis*. In the determination, bioluminescent cells are incubated in milk containing antibiotics for 45 to 60 min followed by an addition of dodecyl aldehyde and an immediate bioluminescence measurement. The result is obtained by comparing the in vivo luminescence value obtained in the presence of antibiotics with a control value obtained in the absence of antibiotics.

The induced test is applied to detect the activity of substances affecting protein synthesis. The test is based on the ability of antibiotics to inhibit the luciferase synthesis in the treated cells. The test uses dark mutants of luminescent bacteria that undergo induction of the luminescence system in the presence of certain DNA-intercalating agents, such as acridine dyes and caffeine. The article describes the use of the *Photobacterium leiognathi* 8SD18 mutant e.g. in the determination of gentamicin.

In the bacteriophage test, a bioluminescent bacterium is infected by a specific bacteriophage. In the absence of antibiotic, the luminescent bacteria are lysed and no in vivo luminescence can be detected. Antibiotics that inhibit DNA, RNA, or protein synthesis also inhibit the phage development and thus the lysis of the bacteria. According to the article, the test can be carried out by using the *Vibrio harveyi* MAV strain which is infected with a bacteriophage $V_1$, or a luminescent *Escherichia coli* which is infected with a bacteriophage $T_5$.

In the tests described above, the result is affected by a great variety of factors, and so the conditions have to be controlled accurately. For instance, problems are caused by the fact that as the luminescent bacteria are marine organisms, they need salt. The concentration of bivalent cations, such as $Ca^{++}$ and $Mg^{++}$, however, has to be controlled very accurately as they are known to inhibit the activity of aminoglycosides, such as streptomycin, kanamycin and erythromycin. The activity of certain antibiotics is highly pH dependent, and therefore the pH should be adjusted specifically for the antibiotic to be determined in each particular case. In the induced test, the induction conditions are extremely critical. In addition to antibiotics the samples may contain other compounds which induce bioluminescence in an uncontrolled manner. In the bacteriophage test, the reaction conditions also have to be adjusted very accurately, and the bacteriophage addition has to made at an appropriate time. One of the most severe drawbacks of the tests is that they cannot be applied for the detection of antibiotics of all types.

The above problems have prevented the use of bioluminescence for the determination of antibiotics or bacteriophages in commercial applications.

Naturally occurring luminescent bacteria are classified into three genera, viz. Vibrio, Photobacterium and Xenorhabdus. Most of them belong to the first two genera and occur mainly in seawater. Luminescent Xenorhabdus species occur in the soil. Luminescent bacteria are gram-negative motile rods, mostly facultatively snaerobic. As the luminescence genes originate from gram-negative organisms, they are not expressed as such in gram-positive organisms.

Streptococci are gram-positive bacteria which are not inherently luminescent. However, a process has now been developed by means of which the bacteria of the Streptococcus species, especially *Streptococcus thermophilus* bacteria, can be made bioluminescent.

*Streptococcus thermophilus* has not previously been used in commercial applications in genetic engineering technology. Although several attempts have been made, genetic engineering techniques have not provided any good results. For *Streptococcus thermophilus*, the prior art methods have proved totally inappropriate. The biggest problem has been that it has not been possible to effect the expression of foreign genes.

For instance, P. Slos, J-C Bourquin, Y. Lemoine, and A. Mercenier describe (Appl. Environ. Microbiol. 57 (1991) 1333–1339) the isolation and characterization of chromosomal promoters of *Streptococcus salivarius subsp. thermophilus*. They also describe the expression of a cat gene causing chloramphenicol resistance. The expression is reported to be too low for a direct resistance selection to be successful. A. Mercenier, the leader of the research group, states in his review article Molecular genetics of *Streptococcus thermophilus*, FEMS Microbiol. Rev. 87 (1990) 61–78, that it has been difficult to find suitable marker genes for this organism. For instance, attempts to apply catechol-2,3-oxygenase have not been successful, even though this is a widely used marker gene in other gram-positive bacteria.

Attempts have also been made to use a genetically modified *S. thermophilus* e.g. for the production of thaumatin, but this has not either been successful. Except for congress posters, there are no documents on the subject as the attempts have failed.

The molecular biology of *S. thermophilus* has thus proved to be extremely difficult, and so this organism has not been regarded as a potential candidate for commercial applications. Also in general, the organism is regarded as a genetically difficult object. Problems are caused by the relatively low and/or poorly reproducible gene transfer frequencies, scarcity of functioning vectors, instability, etc.

However, the genes needed to cause emission of light have now been successfully transferred and expressed even in *S. thermophilus*.

The invention thus relates to bioluminescent *Streptococcus thermophilus* bacteria containing foreign genes causing bioluminescence.

The invention also relates to the use of these *Streptococcus thermophilus* bacteria in the determination of antibiotics and bacteriophages, and to a test set containing the above-mentioned bioluminescent *Streptococcus thermophilus* bacteria.

The invention further relates to processes for the determination of antibiotics and bacteriophages, which processes are based on the measurement of the bioluminescence caused by luminescent *Streptococcus thermophilus* bacteria.

BRIEF DESCRIPTION OF THE FIGURE

FIG. 1 shows the structure of the plasmid pMJ763 containing the luxA and luxB genes of *Xenorhabdus luminescens*. The plasmid pMJ763 contains a) a ClaI-HindIII fragment from the plasmid pKTH1799, which fragment contains a promoter and a signal sequence, b) an EcoRI-SalI fragment containing the luxA and luxB genes of *Xenorhabdus luminescens*, c) a SalI-BamHI fragment containing the rrnB terminator of *E. coli*, and d) a ClaI-EcoRV fragment from the plasmid pVS2.

The *Streptococcus thermophilus* T101 strain having properties suitable for the determination of antibiotics is used as a model organism in the present specification. The strain has been deposited at the Deutsche Sammlung von Mikroorganismen under the deposit number DSM 4022 on Mar. 3, 1987, and it possesses the following properties:

gram positive forms long coccus chains growing temperature:
 growth at 50° C.
 no growth at 10° C.

salt resistance
 growth at a NaCl concentration of 2%
 no growth at a NaCl concentration of 6.5%, titrated acidity 25 to 29 °SH after 7-hour incubation at 42° C. (sterilized 10% milk powder milk)

lactic acid %: 0.8% (incubated for 2 days at 42° C., from milk powder milk)

ferments lactose, sucrose and glucose.

Judging from the values reported in the prior art, this microorganism strain is clearly more sensitive to antibiotics than the other known *Streptococcus thermophilus* strains, especially to penicillin, oxytetracycline and streptomycin.

The *S. thermophilus* T101 strain is modified genetically by adding genes causing the bioluminescence property. Literature describes various genes suitable for the purpose, of which examples were given above. In the present invention, it has been shown that the lux genes of *Vibrio harveyi* and *Xenorhabdus luminescens* are very suitable for the purpose. The lux genes of both organisms can be transferred to streptococci as described herein, and they operate and are expressed in the desired manner, i.e. effect bioluminescence in the above-mentioned bacteria. The results obtained show that it is also possible to use other corresponding genes, if desired. The genes of *Xenorhabdus luminescens*, however, are preferred as it has been found that the luciferase encoded by them has an excellent thermal stability.

In addition to the *S. thermophilus* T 101 strain, other *S. thermophilus* strains have also been used in the examples in order to show the workability and broad applicability of the present invention.

The constructing of the plasmids according to the invention is described in Examples 1 and 2.

The plasmid pTVB61 contains the luxA/B gene fusion of *Vibrio harveyi*. The plasmid contains a) a ClaI-HindIII fragment from the plasmid pVS2 (FI Patent 77056), b) a ClaI-HindIII fragment from the plasmid pKTH1799, which fragment contains a promoter and a signal sequence (Appl. Environ. Microbiol. 57 (1991) 341–348, Sibakov et al.), and c) a BamHI-HindIII fragment from the plasmid pMJ499 containing the luxA/B gene fusion of *Vibrio harveyi* and a transcription terminator (Mol. Gen. Genet. 230(1991) 251–256, Jacobs et al.).

The use of the plasmid pMJ763 containing the *Xenorhabdus luminescens* lux A,B genes coding for thermostable luciferase is regarded as the preferred embodiment of the invention. The plasmid pMJ763 contains a) a ClaI-HindIII fragment from the plasmid pKTH1799, which fragment contains a promoter and a signal sequence (Appl. Environ. Microbiol. 57 (1991) 341–348, Sibakov et al.), b) an EcoRI-SalI fragment containing the luxA and luxB genes of *Xenorhabdus luminescens* (J. Biol. Chem. 265 (1990) 16581–16587, Szittner and Meighen), c) a SalI-BamHI fragment containing the rrnB terminator of E. coli (J. Mol. Biol. 148 (1981) 107–127, Brosius et al.), and d) a ClaI-EcoRV fragment from the plasmid pVS2 (FI Patent 77056).

The plasmids are transformed in Streptococcus thermophilus e.g. by electroporation. Their ability to be expressed in this microorganism is demonstrated by culturing the transformed cells in a suitable culture medium and observing the bioluminescence caused by the lux genes.

The test set is prepared in the following way: The genetically modified microorganism strain is grown in a fermenter at pH 6.2 to 6.5 and at 38° to 42° C. in a culture medium based on whey permeate. The growth is observed and arrested at the end of the logarithmic growth phase, whereafter the culture broth is concentrated by filtrating to a 20-fold concentration. The concentrate is mixed with a protective agent. The protective agent may be any conventional protective agent used in the preparation of lyophilized microbe preparations, or some other substance suited for the purpose, such as sterilized milk. Preferably the protective agent is an aqueous solution comprising 1.1% of sodium glutamate, 1.1% of ascorbic acid, and the pH of which is 6.5. A suitable mixing ratio between the concentrate and the protective agent is e.g. about $4-5\times10^{-2}$, preferably about $5\times10^{-2}$. The concentrate is measured into a vessel which may be a conventional vial, a sealable test tube, a sample bottle, or the like. The vessel is lyophilized and stored under vacuum. The finished test set contains about 1 to $2\times10^6$ bacteria per ml.

The antibiotic determination is carried out by adding a liquid sample to the test set. The test set and the sample are incubated, and an aliquot of the mixture is transferred to a measuring cuvette. A long-chain aldehyde, such as n-decyl aldehyde or dodecyl aldehyde, is added to the cuvette, and the mixture is stirred and measured immediately or after a suitable incubation period. The measuring can be carried out by visually evaluating the intensity of the luminescent light and its deviation from a control. The measuring may also be carried out luminometrically by a suitable device. The result obtained in this way will, of course, be more accurate. If the sample contains antibiotics, the microorganisms in the test set are not able to grow and much less bioluminescence caused by them is detected. If the sample does not contain antibiotics, the microorganisms will grow, and no changes occur in the luminescence values.

Naturally, the antibiotic determination can also be carried out by using a fresh culture of a bioluminescent Streptococcus thermophilus. A liquid sample is then added to the fresh culture, incubated and transferred to a measuring cuvette, after which the same procedure as outlined above is adopted.

The bacteriophage determination can also be carried out by using a fresh culture of a bioluminescent Streptococcus thermophilus or by using the test set described above. The determination is carried out by adding a liquid sample to the fresh culture or the test set. After incubation, an aliquot of the mixture is transferred to a measuring cuvette. A long-chain aldehyde, such as n-decyl aldehyde or dodecyl aldehyde, is added to the cuvette, and the mixture is stirred and measured immediately or after a suitable incubation period. The measuring can be carried out by visually evaluating the intensity of the luminescent light and its deviation from a control. The measuring may also be carried out luminometrically by a suitable device. The result obtained in this way will, of course, be more accurate. If the sample contains bacteriophages, the microorganisms in the test set are lysed and much less bioluminescence is detected. If the sample does not contain bacteriophages, the microorganisms will grow, and no changes occur in the luminescence values.

The antibiotic sensitivity of the processes based on the use of the S. thermophilus T101 strain and the T102 strain containing the plasmid pMJ763 has been compared with the corresponding commercial THERMOCULT (Orion Diagnostica) and DELVOTEST P and DELVOTEST SP (Gist-Brocades) techniques based on Bacillus stearothermophilus strains. The determinations were performed according to the suppliers' instructions. For the T102 strain, the antibiotic determinations were performed as described in Example 5 of the present application. The results are presented in Table 1, which also shows the data supplied by the manufacturer Intervet concerning the INTERTEST. The results show that the processes based on the S. thermophilus strains T101 and T102 are superior to the other processes in both sensitivity and broadness of spectrum.

It is also to be seen that the genetical modification of the S. thermophilus T101 strain has no disadvantageous effect on the antibiotic sensitivity properties. For several important antibiotics, the results obtained by the new strain T102 were even better than those obtained by the original strain T101. Penicillin G, cloxacillin, dicloxacillin and amoxycillin may be mentioned as examples. As to neomycin, tetracycline and oxytetracycline, slightly lower sensitivities were measured. It has been shown by genetic engineering techniques that the sensitivity properties of the microorganism with respect to these antibiotics have not changed. The inferior results can be attributed to the fact that the described determination process is not optimized for these antibiotics.

TABLE 1

Antibiotic sensitivity of processes based on the use of different Bacillus stearothermophilus (Delvotest, Thermocult disc technique) and Streptococcus thermophilus (Intertest, T101-TEST and T102) strains

| Antibiotic | | T101-Valiotest | T102 | DELVOTEST P | DELVOTEST SP | THERMOCULT | INTERTEST[a] |
|---|---|---|---|---|---|---|---|
| G-penicillin | IU/ml | 0.004–0.006 | 0.004–0.005 | 0.003–0.005 | 0.003 | 0.003–0.005 | 0.005 |
| Ampicillin | µg/ml | 0.01 | 0.015–0.02 | 0.01 | | 0.01 | 0.005 |
| Amoxycillin | " | 0.03–0.05 | 0.03–0.04 | | | | |
| Cloxacillin | " | 0.1–0.15 | 0.1–0.2 | 0.05 | 0.2 | | |
| Dicloxacillin | " | 0.1–0.15 | 0.15–0.2 | | | | |
| Oxacillin | " | 0.15–0.2 | 0.2–0.3 | | | | |
| Cephalexin | " | 0.05–0.1 | 0.04–0.05 | | | | |
| Cephapirin | " | 0.05–0.1 | 0.01–0.015 | | | | |
| Ceftiofur | " | 0.02 | 0.05 | | | | |
| Streptomycin | " | 1.0–1.5 | 1.3–1.4 | 3.75–5.0 | | 3.75–5.0 | 5.0 |

TABLE 1-continued

Antibiotic sensitivity of processes based on the use of different *Bacillus stearothermophilus* (Delvotest, Thermocult disc technique) and *Streptococcus thermophilus* (Intertest, T101-TEST and T102) strains

| Antibiotic | | T101-Valiotest | T102 | DELVOTEST P | DELVOTEST SP | THERMOCULT | INTERTEST[a] |
|---|---|---|---|---|---|---|---|
| Dihydrostreptomycin | " | 1.0–1.5 | 1.2–1.3 | 2.5–5.0 | | 2.5–5.0 | |
| Erythromycin | " | 0.05–0.1 | 0.05–0.2 | 0.5–1.0 | | 0.5–1.0 | 0.1 |
| Neomycin | " | 0.3–0.5 | 0.7–1.3 | 1.0 | | 3.0 | 20.0 |
| Chloroamphenicol | " | 0.5–1.0 | | 10.0 | 9.0 | 7.5–10.0 | 1.0 |
| Tetracycline | " | 0.2–0.3 | 0.8–2.0 | 0.2–0.3 | 0.6 | 1.0–2.0 | 0.5 |
| Oxytetracycline | " | 0.15–0.2 | 0.3–0.8 | 0.2 | 0.3–0.6 | 1.0–2.0 | 0.2 |
| Spiramycin | " | 0.15–0.3 | 0.3–0.4 | 5.0 | 1.0–2.0 | | |

[a] Concentrations given by the manufacturer

The examples to be given below are intended to illustrate the invention, whereas they are not intended to limit the scope of the invention.

EXAMPLE 1

Construction of the plasmid pTVB61

2 μg of DNA from the plasmid pVS2 (FI 77056) in TE buffer (10 mM Tris—1 mM EDTA, pH 8.0) were digested with the ClaI (5 U) and HindIII (5 U) enzymes; the digestion mixture contained 1/10 of B buffer (Boehringer Mannheim, the final concentration 10 mM Tris—5 mM $MgCl_2$—100 mM NaCl—1 mM 2-mercaptoethanol, pH 8.0), incubation at +37° C. for 4 h. The fragments were separated in a 0.8% agarose gel, and a fragment of about 4 kb was excised. The fragment was crushed in an Eppendorff tube, 250 μl of TE buffer and 500 μl of phenol were added. The tube was frozen in liquid nitrogen and centrifuged at 12,000 rpm for 15 min at room temperature. The aqueous phase was recovered and purified by phenol and chloroform-isoamyl alcohol (24:1) extraction followed by ethanol precipitation. The fragment was dissolved in TE buffer.

5 μg of DNA from the plasmid pKTH1799 (Appl. Environ. Microbiol. 57 (1991) 341–348, Sibakov et al.) in TE buffer were digested with the ClaI and HindIII enzymes similarly as above. A 400 bp fragment was separated from the agarose gel as described above.

0.3 μg of the 4 kb ClaI-HindIII fragment and 0.1 μg of the 0.4 kb fragment were mixed together, 1/10 of ligation buffer (Boehringer Mannheim, 660 mM Tris—50 mM $MgCl_2$—10 mM DTE—10 mM ATP, pH 7.5) was added while the total volume was 20 μl. 1 U of T4 DNA ligase was added and the ligation mixture was incubated at +16° C. for 16 hours. The ligation mixture was precipitated with ethanol and dissolved in 5 μl of TE buffer.

*Lactococcus lactis* MG1614 cells were subjected to electroporation (Appl. Environ. Microbiol. 55 (1989) 3119–3123, Holo and Nes) with 3 μl of ligation DNA, and the transformants were selected on M17 plates containing 0.5% of glucose and 5 μg/ml of chloramphenicol. Plasmid separation from the transformants was carried out according to Anderson and McKay (Appl. Environ. Microbiol. 46 (1983) 549–552). The plasmid construction was named pVS22.

2 μg of DNA from the plasmid pVS22 were digested in B buffer with the HindIII and EcoRV enzymes and separated from the gel (a 4.4 kb fragment) as described above.

2 μg of DNA from the plasmid pMJ499 (Mol. Gen. Genet. 230 (1991) 251–256, Jacobs et al.) were digested in B buffer with the BamHI enzyme as described above in a volume of 20 μl. After digestion 1 μl of each dNTP (0.5 mM solutions) and 5 U of Klenow enzyme were added to the mixture followed by incubation at +30° C. for 15 min. The reaction was arrested at +75° C., 10 min. HindIII enzyme was added to the mixture, whereafter it was digested and a 2.5 kb fragment was separated from the gel as described above.

200 ng of the pVS22 HindIII-EcoRV fragment and 200 ng of the pMJ499 (BamHI)-HindIII fragment were ligated, subjected to electroporation, selected, and the plasmid separation was carried out as described above. This plasmid construction was named pTVB61.

EXAMPLE 2

Construction of the plasmid pMJ763

*Xenorhabdus luminescens* was grown and chromosomal DNA was isolated as described in J. Bacteriol. 173 (1991) 1399–1405, Xi et al.

The luxA and luxB genes from the *X. luminescens* ATCC 29999 strain were amplified in the following way. 100 ng of chromosomal DNA from *X. luminescens*, 100 pmol of the 5' end primer of the luxA (Biotech. and Appl. Biochem. 17 (1993) 3–14, Hill et al.), 100 pmol of the 3'-end primer 5'CTCGTCGACATTCGTTCACTT3' of the luxB, 1/10 of the volume of a reaction buffer (500 mM KCl—100 mM Tris, pH 8.5—15 mM $MgCl_2$—0.1% gelatin), each dNTP in an amount such that the final concentration was 60 μM, and 5 U of Taq DNA polymerase were introduced into the mixture. The final volume of the mixture was 100 μl. Denaturation at 95° C. for 1 min; annealing at 55° C. for 1 min; elongation at 72° C. for 1 min; 29 cycles. After amplification, the mixture was purified by using phenol and a chloroform-isoamyl alcohol extraction followed by ethanol precipitation.

1 μg of the amplified fragment (in 20 μl of TE buffer) was added to 1/10 of H buffer (Boehringer Mannheim, the final concentration 50 mM Tris—10 mM $MgCl_2$—100 mM NaCl—1 mM DTE, pH 7.5), 5 U of EcoRI enzyme was added followed by incubation at +37° C. for 4 h. 1 μl of each dNTP (0.5 mM solutions) and 5 U of Klenow enzyme were added to the mixture followed by incubation and reaction arrest as above. 5 U of SalI enzyme was added to the mixture followed by digestion and purification as above.

2 μg of DNA from the plasmid pTVB61 were digested in B buffer with HindIII enzyme as described above. 1 μl of each dNTP (0.5 mM solutions) and 5 U of Klenow enzyme were added to the mixture followed by incubation and reaction arrest as above. The mixture was purified by phenol and chloroform-isoamyl alcohol (24:1) extractions, and ethanol precipitation. The DNA was dissolved in 20 μl of TE buffer, 1/10 of H buffer and 5 U of SalI enzyme were added followed by incubation as described above. A 5 kb fragment was separated from the gel as described above. The amplified fragment (EcoRI)-SalI and the 5 kb (HindIII)-SalI fragment from pTVB61 were ligated as above. Electroporation, selection and plasmid separation were carried out as described above. This plasmid construction was named pMJ763.

EXAMPLE 3

Transformation of *S. thermophilus*

Cells of the *S. thermophilus* T101 (DSM 4022) strain were grown in M17 broth containing 2% of lactose at 42° C. for about 7 hours. A 1–2% inoculum was taken from the culture into M17 broth containing 5% of sucrose, 2% of lactose and 0.2% of glycine. The culture was grown until the $OD_{600}$ value was 0.6. The cells were harvested by centrifugation and then washed twice with a solution containing 5% of sucrose and 15% of glycerol. The cell pellet was suspended in the above-mentioned washing buffer to a volume which was 1/200 of the volume of the original culture. 100 µl of the cell suspension was cooled in an ice bath, the plasmid DNA was added, and the mixture was transferred into an ice-cold electroporation cuvette. The electroporation was carried out in a 0.2 cm cuvette at 25 µF, 1,000 ohm, 2.0 kV (Bio-Rad, Gene Pulser). After electroporation the cells were transferred immediately into an expression broth (M17 broth containing 5% of sucrose, 2% of lactose, 2 mM $CaCl_2$ and 20 mM $MgCl_2$), and they were expressed at 42° C. for 2 to 3 hours. The cells were plated on M17 agar to which 2% of lactose and 5 µg/ml of chloramphenicol had been added. The plates were incubated at 42° C. for 1 to 2 days. A chloramphenicol resistant colony was transferred to a M17 broth containing 2% of lactose and 5 mg/ml of chloramphenicol for culturing at 42° C. for 12 to 16 hours, and then a 2% inoculum was taken from it into the above-mentioned broth followed by incubation for about 4 hours.

1 ml of the culture containing the plasmid pMJ763 was introduced into a measuring cuvette followed by an addition of 40 µl of 0.1% n-decylaldehyde (in 50% ethanol), mixing and immediate luminescence measuring.

To measure the bioluminescence from the strain containing the plasmid pTVB61, the culture was incubated at 42° C. for 4 hours, at +30° C. for 30 min, whereafter measuring was carried out as described above.

When measured as described above, the plasmids pTVB61 and pMJ763 in the *S. thermophilus* T101 host emit more than 1,000 RLU (Relative Light Units). The *S. thermophilus* T101 strain containing the plasmid pMJ763 is called T102 and the strain containing the plasmid pTVB61 is called VS796.

*Streptococcus thermophilus* T102 was deposited at the Deutsche Sammlung von Mikroorganismen und Zellkulturen GmbH, Mascheroder Weg 1b, D-38124 Braunschweig, in accordance with the Budapest Treaty under the deposit number DSM 8411 on Jul. 5, 1993. Strain VS796, which includes plasmid pTVB61, has also been deposited at the Deutsche Sammlung von Mikroorganismen und Zellkulturen GmbH, Mascheroder Weg 1b, D-38124 Braunschweig, in accordance with the Budapest Treaty under Accession Number DSM 11194 on Sep. 27, 1996.

EXAMPLE 4

Preparation of the test set

Bacteria of the bioluminescent *Streptococcus thermophilus* strain, e.g. the T102 strain or VS796 strain were inoculated in a culture medium having the following composition:

5% of whey permeate powder 1.5% of casein hydrolysate 0.5% of tryptone

1% of yeast extract

The culture medium had been sterilized at 120° C. for 15 to 20 min, and its pH was 6.4 after the sterilization.

The test strain was grown in a fermenter at a pH of about 6.2 at about 42° C., and the growth was monitored by observing the turbidity of the culture broth. At the end of the logarithmic growth phase the growth was arrested and the culture broth was concentrated by filtration using a Millipore Pellicon filtration unit (0.45 µm) to a 20-fold concentration, whereby the bacterium concentration of the concentrate was about $2 \times 10^9$ bacteria per ml. The concentrate was washed with a small amount of protective agent, and about 5 ml was added to 100 ml of the protective agent. The protective agent was an aqueous solution containing 1.1% of sodium glutamate and 1.1% of ascorbic acid and having a pH of 6.5. The bacterium concentration of the solution so obtained was about $1 \times 10^8$ bacteria per ml. 1 ml of the solution was added to a conventional 10 ml vial withstanding drying and closeable by vacuum. The vial was freeze dried and vacuum closed for storage. The vial thus prepared contained 1 to $2 \times 10^6$ bacteria per ml.

EXAMPLE 5

Determination of antibiotics in a milk sample by using the T102 strain

Raw milk samples and antibiotic-free control raw milk were tempered to 22° C. 2 ml of milk was added to the test set prepared as described in Example 4, stirred and incubated at 42° C. for 1.5 to 2 hours. The background value given by the test sets was measured in the same way but after 15 min of incubation. After incubation the test sets were stirred and 1 ml of the solution was transferred into measuring cuvettes. 40 µl of 0.3% n-decylaldehyde (in 50% ethanol) was added to the cuvettes, the solution was stirred and allowed to stand at room temperature for 5 min and then measured by a luminometer. The 15-min background value was subtracted from the RLU value of the samples and the control, whereafter the value of the sample was compared with the value of the control. The sample contains antibiotic if the value has decreased 50% from the control value.

EXAMPLE 6

Determination of antibiotics in a milk sample by using the VS796 strain

Raw milk samples and antibiotic-free control raw milk were tempered to 22° C. 2 ml of milk was added to the test sets prepared as described in Example 4, stirred and incubated at 42° C. for 1.5 to 2 hours, whereafter they were transferred to 30° C. for 30 min. After incubation the test sets were stirred and 1 ml of the solution was transferred into measuring cuvettes. 40 µl of 0.3% n-decylaldehyde (in 50% ethanol) was added to the cuvettes, the solution was stirred and allowed to stand at room temperature for 5 min and then measured by a luminometer. The sample contains antibiotic if the value has decreased 50% from the control value.

EXAMPLE 7

Determination of antibiotics in a meat juice sample by using the T102 strain

The test set was prepared as described in Example 4 by using sterilized 10% milk powder milk containing 1.1% of sodium glutamate and having pH 6.5 as a protective agent.

Meat juice was separated from meat by a freeze and thaw treatment. The meat juice sample and an antibiotic-free control meat juice sample were tempered to 22° C. 2 ml of meat juice were added to the test set followed by stirring and incubation at 42° C. for 1.5 to 2 hours.

The background value given by the test set was measured in the same way but after 15 min of incubation measured in the same way but after 15 min of incubation. After incubation the test sets were stirred and 1 ml of the solution was transferred into measuring cuvettes. 40 µl of 0.1% n-decylaldehyde (in 50% ethanol) was added to the cuvettes, the solution was stirred and allowed to stand at room temperature for 5 min and then measured by a luminometer. The 15-min background value was subtracted from the RLU value of the sample and the control, whereafter the value of the sample was compared with the value of the control. The sample contains antibiotic if the value has decreased 50% from the control value.

EXAMPLE 8

Determination of bacteriophages in milk by using the T102 strain

A milk sample containing a bacteriophage was introduced on ready fresh or cold-dried (test set) T 102 and incubated at 42° C. The result was read e.g. after 2 or 3 hours. If the sample contains bacteriophage, the bioluminescence decreases or dies out entirely. Table 2 shows results obtained by determining five phages effective on *Streptococcus thermophilus* T101 and concentrations that can be traced by the test in 1) two hours and 2) three hours.

TABLE 2

Determination of bacteriophage by using the *Streptococcus thermophilus* T102 strain

| phage | 1367 | 1368 | 1998 | 1999 | 2000 |
|---|---|---|---|---|---|
| 1) | $1.1 \times 10^4$ | $2.4 \times 10^4$ | $1.8 \times 10^4$ | $1.8 \times 10^4$ | $3.5 \times 10^3$ |
| 2) | $1.1 \times 10^3$ | $2.4 \times 10^3$ | $1.8 \times 10^3$ | $1.8 \times 10^3$ | $3.5 \times 10^2$ |

The results shown in Table 2 have been obtained by using a fresh *Streptococcus thermophilus* culture. When a cold-dried sample is used, i.e. the set test prepared as described in Example 4, the values fall from those shown in the table by one logarithm. The sensitivity of determination is thus clearly below $10^5$ pfu/ml, which is essential from the viewpoint of the dairy industries; if raw milk contains $10^5$ pfu/ml, the failure of the industrial process can be expected. It is further to be noted that the test result is easy to read: the bioluminescence falls very abruptly to a level 10 to 100 times lower, almost down to the zero.

EXAMPLE 9

Determination of bacteriophages in milk and whey by using several different bioluminescent *Streptococcus thermophilus* strains In this example, six *Streptococcus thermophilus* starter strains were examined, into each one of which the plasmid pMJ763 had been transferred as described in Example 3. These bioluminescent bacteria were then exposed to a milk or whey sample to be analysed either fresh or cold-dried as described above. The cold-drying process, i.e. the preparation of the test set, is similar to that described in Example 4 for T102 cells.

The results are shown in Table 3.

TABLE 3

Determination of bacteriophages by using different *Streptococcus thermophilus* strains

| S. thermophilus strain | phage | phage concentration* fresh | phage concentration* cold-dried | time |
|---|---|---|---|---|
| code 12 | φ H1 | $10^7$ | nd | 2 h |
|  |  | $10^4$ | $10^3$–$10^4$ | 3 h |
| code 7 | φ F6 | (−2 dilut.) | nd | 2 h |
|  |  | −2 dilut. | −2 dilut. | 3 h |
| code 89 | φ V4 | $10^5$ | nd | 2 h |
|  |  | $10^4$ | $10^3$ | 3 h |
| code 91 | φ F6 | (−2 dilut.) | nd | 2 h |
|  |  | −2 dilut. | −2 dilut. | 3 h |
| code 704 | φ 638 | $10^6$ | nd | 2 h |
|  |  | $10^5$ | $10^6$ | 3 h |
| code 807 | φ 600 | $10^3$ | $10^4$ | 2 h |
|  |  | $10^1$ | below $10^4$ | 3 h |

*phage concentration that could be detected in the time used
−2 dilut. means that the plating of the phage has not been possible, but the effect could be seen in a test tube already at this dilution.

In short, sufficiently small phage amounts could already be traced in three hours. Decrease in luminescence is also extremely clear, so that the test result is easy to read. Luminescence values fall to a level 10 to 100 times lower.

We claim:

1. A bioluminescent *Streptococcus thermophilus* strain comprising a plasmid selected from the group consisting of pMJ763 and pTVB61.

2. The strain according to claim 1 wherein said strain is *Streptococcus thermophilus* T102 having Accession Number DSM 8411.

3. The strain according to claim 1 wherein said strain is *Streptococcus thermophilus* VS796 having Accession Number DMS 11194.

4. A test kit comprising a bioluminescent *Streptococcus thermophilus* strain comprising a plasmid selected from the group consisting of pMJ763 and pTVB61, and a suitable protective agent.

5. The test kit according to claim 4, wherein the strain is *Streptococcus thermophilus* T102 having Accession Number DSM 8411 or *Streptococcus thermophilus* VS796 having Accession No. DMS 11194.

6. The test kit according to claim 4 wherein the protective agent is an aqueous solution comprising 1.1% sodium glutamate and 1.1% ascorbic acid and having a pH of about 6.5.

7. The test kit according to claim 4 wherein the protective agent is milk or an aqueous solution containing 10% powder milk, each comprising 1.1% sodium glutamate and having a pH of about 6.5.

8. The test kit according to claim 4 wherein the concentration of cells of said strain is about $1 \times 10^6$ to $2 \times 10^6$ bacteria per ml.

9. The test kit according to claim 4 wherein cells of said bioluminescent *Streptococcus thermophilus* strain are used as a concentrate, the dilution ratio between the concentrate and the protective agent being about $4 \times 10^{-2}$ to $5 \times 10^{-2}$.

10. A process of detecting the presence of an antibiotic in a liquid sample comprising:

i) adding said liquid sample to a culture of a bioluminescent *Streptococcus thermophilus* strain comprising a plasmid selected from the group consisting of pMJ763 and pTVB61, or to a test kit comprising cells of said strain, and a suitable protective agent;

ii) incubating the mixture resulting from step (i) for about 1 to 2 hours at about 38° C.–42° C.;

iii) adding a long-chain aldehyde to the mixture; and iv) measuring bioluminescence.

11. The process according to claim 10 wherein said strain is *Streptococcus thermophilus* T102 having Accession Number DSM 8411 or *Streptococcus thermophilus* VS796 having Accession No. DMS 11194.

12. The process according to claim 10 wherein said liquid sample is milk or meat juice.

13. A process of detecting the presence of bacteriophage in a liquid sample comprising:

i) adding a liquid sample to a culture of a bioluminescent *Streptococcus thermophilus* strain comprising a plasmid selected from the group consisting of pMJ763 and pTVB61, or to a test kit comprising cells of said strain, and a suitable protective agent;

ii) incubating the mixture resulting from step (i) for about 1 to 3 hours at about 38° C.–42° C.;

iii) adding a long-chain aldehyde to the mixture; and iv) measuring bioluminescence.

* * * * *